United States Patent
Singh et al.

(10) Patent No.: US 7,327,896 B1
(45) Date of Patent: Feb. 5, 2008

(54) TESTING APPARATUS AND METHOD FOR A SPECTRAL IMAGING SYSTEM

(75) Inventors: Narsingh B. Singh, Ellicott City, MD (US); Tracy-Ann Waite, Owings Mills, MD (US); David Kahler, Arbutus, MD (US); Andre Berghmans, Owings Mills, MD (US)

(73) Assignee: Northrop Grumman Corporation, Los Angeles, CA (US)

( * ) Notice: Subject to any disclaimer, the term of this patent is extended or adjusted under 35 U.S.C. 154(b) by 664 days.

(21) Appl. No.: 10/940,638

(22) Filed: Sep. 15, 2004

Related U.S. Application Data

(63) Continuation-in-part of application No. 10/916,484, filed on Aug. 12, 2004.

(51) Int. Cl.
*G06K 9/40* (2006.01)

(52) U.S. Cl. ............... 382/260; 359/308; 359/305; 703/5; 703/20

(58) Field of Classification Search ......... 382/191, 382/260; 359/305, 308, 309; 703/5, 20
See application file for complete search history.

(56) References Cited

U.S. PATENT DOCUMENTS

| | | | | |
|---|---|---|---|---|
| 6,490,075 | B1 * | 12/2002 | Scheps et al. | 359/285 |
| 6,771,798 | B1 * | 8/2004 | Haas et al. | 382/103 |
| 6,813,380 | B1 * | 11/2004 | Sola et al. | 382/191 |

* cited by examiner

*Primary Examiner*—Samir Ahmed
*Assistant Examiner*—Eric Rush
(74) *Attorney, Agent, or Firm*—Andrews Kurth LLP

(57) ABSTRACT

A hyperspectral imaging system is tested in the lab to allow a determination of its response to the emission from a simulated target, of certain wavelengths of radiation which the imaging system will be using during target determination. A broadband IR wavelength generator is used to generate a multiplicity of wavelengths representing the target and an emissions simulator is used to generate wavelengths representing target emission of hot gases. An AOTF is used to delete one or more target wavelengths, and to add one or more emission wavelengths, from and to the transmission path to the imaging system.

7 Claims, 5 Drawing Sheets

TESTING APPARATUS AND METHOD FOR A SPECTRAL IMAGING SYSTEM

CROSS-REFERENCE TO RELATED APPLICATIONS

This application is a continuation-in-part of copending application Ser. No. 10/916,484, filed on Aug. 12, 2004 (Case 1215-0529PUS1 {000680-078}).

BACKGROUND OF THE INVENTION

1. Field of the Invention

The invention in general relates to spectral imaging systems and more particularly to testing apparatus for testing a hyperspectral imaging system under various atmospheric or other environmental conditions.

2. Description of Related Art

A popular form of imaging system is the hyperspectral imaging system whereby a region of interest is examined utilizing a plurality of filters which allow respective wavelengths of radiation to sequentially or simultaneously impinge upon a detector array. This technique allows identification of certain desired aspects of the region.

For example, such systems may be used by the military to detect various predetermined targets. The systems also find use in the commercial and environmental fields for determining, by way of example, certain weeds, vegetation, blight, mineral detection, hazardous waste, and soil erosion. The foregoing is but a small sample of the use to which these systems are put.

Generally the signature of a desired feature is known by prior data acquisition before the system is utilized in the field, such that only specific wavelength filters need be employed for the detection process. The response of the system is tested in the laboratory prior to deployment.

However, under actual use in the field, various atmospheric conditions may occur such that one or more wavelengths radiated from the region under investigation, and used in the detection process, will be absorbed, either partially or totally. In addition, certain targets may emit atmospheric radiation such as hot exhaust gases. Therefore to have a viable hyperspectral imaging system, it is necessary to know, a priori, the response of the system under conditions where certain useful wavelengths may be absorbed or generated. The present invention provides a solution to this problem.

SUMMARY OF THE INVENTION

Testing apparatus for testing a spectral imaging system is described and includes a wavelength generator for providing radiation over a broad spectrum and representing a target. An electronically controlled selective filter arrangement is positioned relative to the wavelength generator to pass only certain wavelengths of radiation to the spectral imaging system along a transmission path. The electronically controlled selective filter arrangement includes a control to remove or add a predetermined portion of one or more selected wavelengths from the transmission path. An emissions simulator is operable to generate radiation over a broad spectrum in a predetermined chosen pattern representing emissions from the target, with the emissions simulator being positioned to project its radiation of the chosen emissions pattern, to the electronically controlled selective filter arrangement. The control is operable to select a predetermined one or more wavelengths from the emissions simulator for transmission along the transmission path.

A method of testing a spectral imaging system includes the steps of generating a broad spectrum of wavelengths in a predetermined pattern of a desired target and directed toward the spectral imaging system along a transmission path; interposing an electronically controlled selective filter arrangement to pass only certain wavelengths to the spectral imaging system along the transmission path; controlling the selective filter arrangement to remove or add a predetermined portion of one or more selected wavelengths from the transmission path; generating an additional broad spectrum of wavelengths in a predetermined pattern representing an emission pattern from the target, and projected to the selective filter arrangement; and controlling the selective filter arrangement to select one or more wavelengths from the additional broad spectrum of wavelengths for transmission along the transmission path.

Further scope of applicability of the present invention will become apparent from the detailed description provided hereinafter. It should be understood, however, that the detailed description and specific example, while disclosing the preferred embodiment of the invention, is provided by way of illustration only, since various changes and modifications within the spirit and scope of the invention will become apparent to those skilled in the art, from the detailed description.

BRIEF DESCRIPTION OF THE DRAWINGS

The present invention will become more fully understood from the detailed description provided hereinafter and the accompanying drawings, which are not necessarily to scale, and are given by way of illustration only, and wherein.

DESCRIPTION OF THE PREFERRED EMBODIMENT

Figure 1:
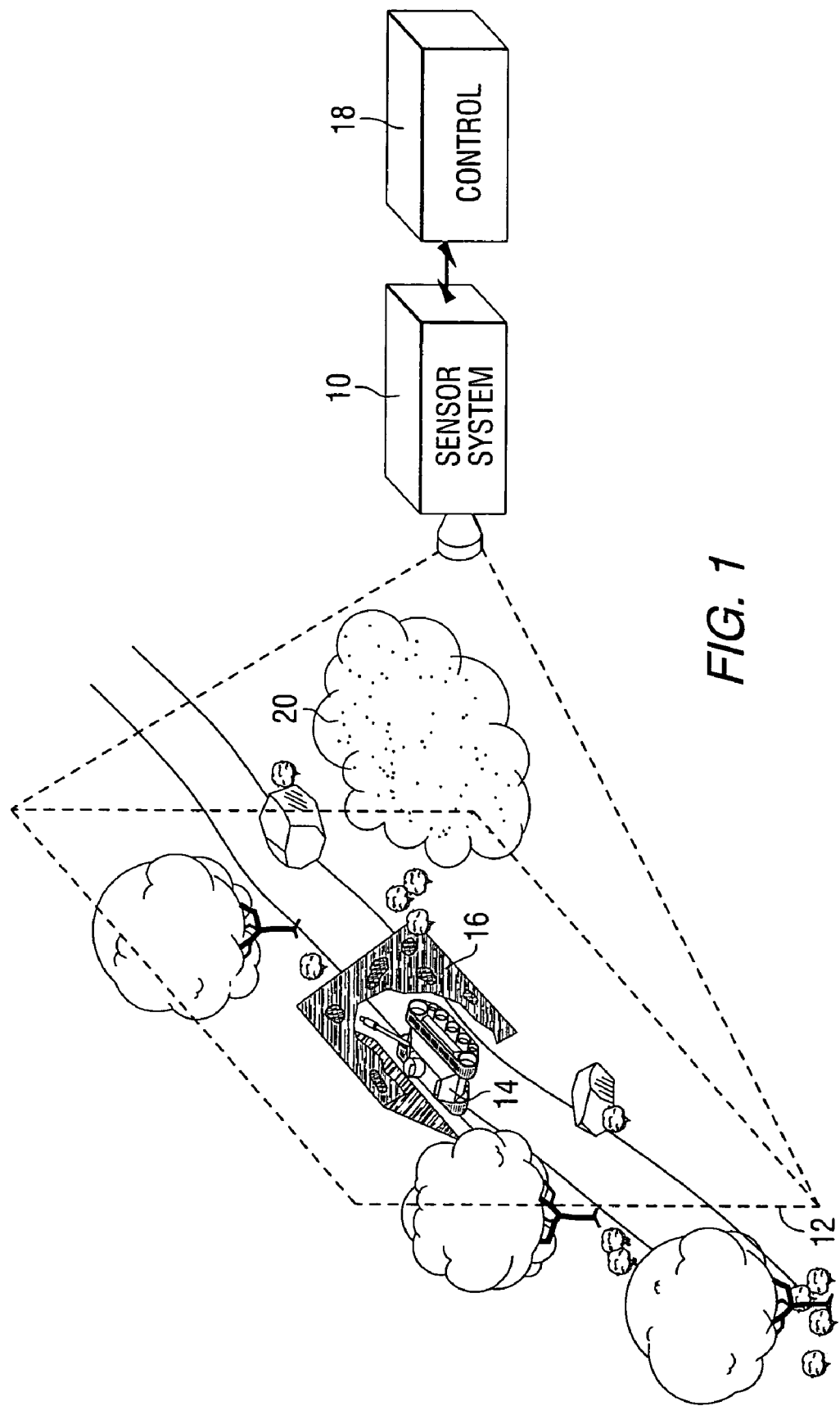
FIG. 1 is a representation of target detection by a hyperspectral imaging system.

In FIG. 1 a sensor system 10 views a region of interest 12 in search of a target 14 which may not be seen due to a covering camouflage 16. A well-known type of sensor system 10 which may be utilized is a spectral sensor system such as a hyperspectral imaging system.

Basically, in such system the region of interest is viewed through a multiplicity of different wavelength filters placed in the path of incoming radiation by a control 18, which will also provide an indication of target location. Typically this filtering operation may be accomplished by a device known as an AOTF (acoustic-optical tunable filter) which will pass radiation of a certain wavelength as a function of an applied control signal.

Although the region of interest is radiating a multiplicity of wavelengths, from prior knowledge, only predetermined ones of those wavelengths need be examined to determine target location. Thus, the control 18 supplies control signals to pass only those wavelengths of interest, either sequentially or simultaneously.

Figure 2:
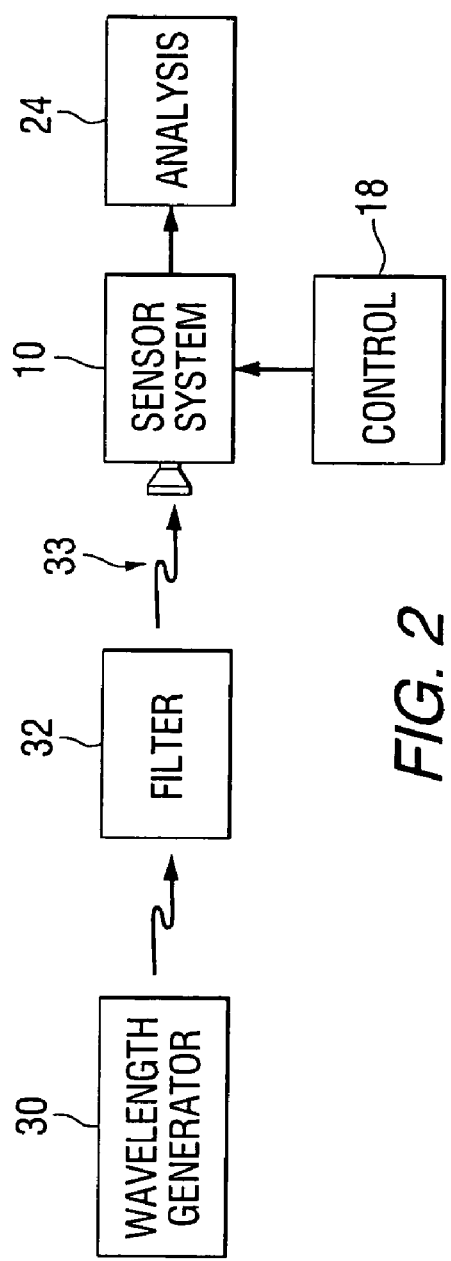
FIG. 2 is a generic block diagram of a hyperspectral imaging system testing apparatus.

A situation may arise, however, that during field use, an atmospheric anomaly may be created between the sensor system 10 and region of interest 12. This anomaly, shown as a cloud 20, may be pollutants, carbon dioxide or other gasses, by way of example. A problem arises in that a particular gas may actually absorb certain wavelengths, including one or more wavelengths used in the target detection process. It is therefore imperative that the response of the sensor system be known in the presence of wavelength absorbing gasses, prior to field use. FIG. 2 is a block diagram of testing apparatus which provides a solution to this problem.

In FIG. 2, the sensor system 10 is brought to a lab for testing prior to deployment in the field. An analysis circuit 24 is provided to determine the response of the sensor system 10 to certain modified and unmodified wavelengths and accomplishes this analysis according to well-known algorithms, not part of the present invention.

The testing apparatus includes a wavelength generator 30 and an electronically controlled selective filter arrangement 32. For hyperspectral imaging in the IR region, the wavelength generator 30 may be comprised of an X-Y array of individual broadband IR pixel emitters which can be individually controlled to emit the same or different energies so that the shape of a particular target may be generated.

The electronically controlled selective filter arrangement 32 selectively controls the wavelengths which will be transmitted to the sensor system 10 via transmission path 33. In one embodiment, only those wavelengths used in the determination of a known target will be transmitted, with one or more of those wavelengths being modified in intensity to simulate the atmospheric absorption. This embodiment is illustrated in FIG. 3.

Figure 3:
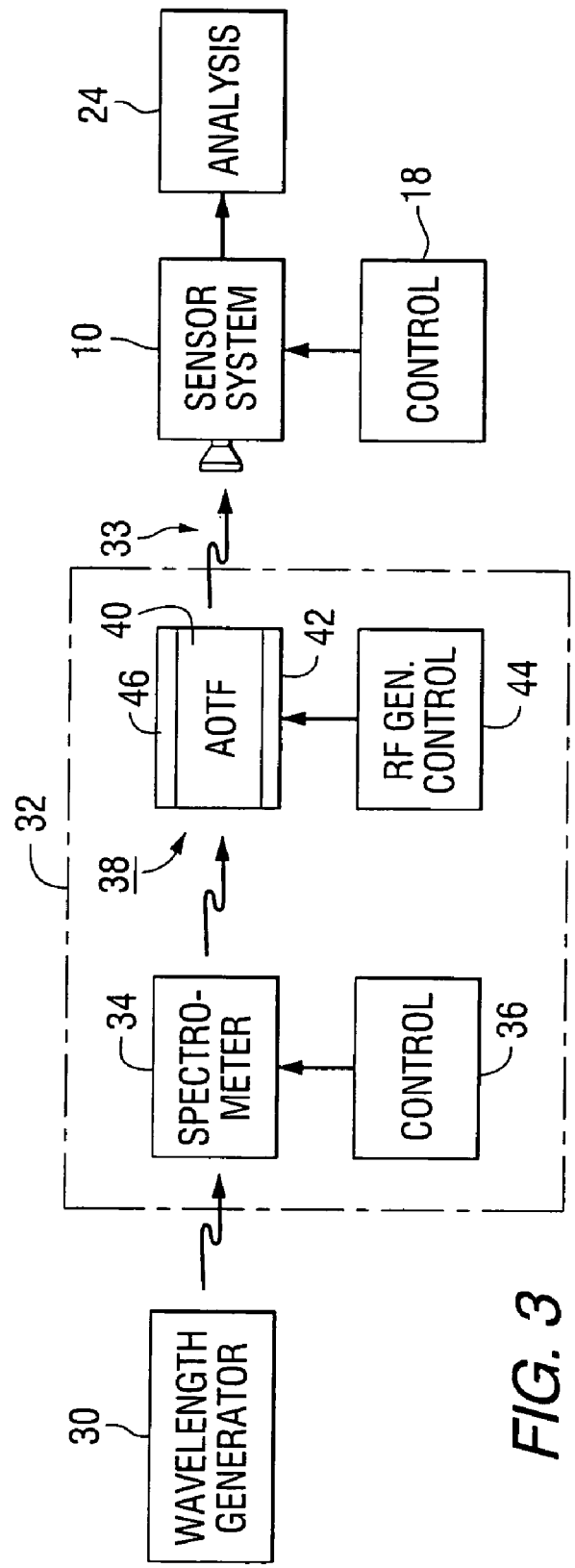
FIG. 3 is a block diagram of one embodiment of the hyperspectral imaging system testing apparatus.

The electronically controlled selective filter arrangement 32 in FIG. 3 includes, in addition to the wavelength generator 30, a spectrometer 34 which will pass only those wavelengths determined by an operator input to control 36. If, for example, it has been determined that wavelengths $\lambda_{12}$, $\lambda_{85}$, $\lambda_{115}$ and $\lambda_{400}$ out of the totality of wavelengths generated by wavelength generator 30 are sufficient to determine a particular target of interest, spectrometer 34 will pass only those wavelengths.

The wavelengths $\lambda_{12}$, $\lambda_{85}$, $\lambda_{115}$ and $\lambda_{400}$ may be transmitted to the sensor system 10 unmodified, to obtain a baseline reading simulating the absence of atmospheric absorption. To simulate atmospheric absorption, another filter is included. This latter filter takes the form of AOTF 38. AOTF 38 includes a birefringent crystal 40 such that, as will be seen, radiation passing through the crystal 40 may take two paths, one straight through with the other path being deflected.

A transducer 42 is bonded to a surface of the crystal 40 and is supplied with an RF signal from RF control circuit 44. This RF signal causes transducer 42 to launch an acoustic shear wave into the crystal 40 where the acoustic shear wave interacts with the radiation entering the crystal 40 and causes a diffraction of radiation of a particular wavelength, depending on the frequency of the applied RF signal. The degree, or amount of such diffraction is a function of the power level of the RF signal. In order to eliminate reflective acoustic waves, an acoustic absorber 46 is bonded to the crystal 40 on a side opposite that of transducer 42.

After a baseline determination has been obtained for the sensor system 10, atmospheric absorption may then be simulated to obtain the response of the sensor system 10 under such circumstances. This is accomplished by having the RF control circuit 44 apply the necessary RF signal to totally or partially deflect a selected one of the wavelengths, the one which is absorbed by the atmospheric gas, for example $\lambda_{115}$. The amount of absorption, from partial to total, is governed by the power level assigned by RF control circuit 44. Thus at the sensor system 10 location an absorption scenario whereby $\lambda_{115}$ has been modified, is reproduced. The amount of simulated absorption may, if desired, be varied from 0% to 100% for test purposes.

Although the previous example described the modification of a single wavelength, it is possible to so modify a plurality of wavelengths either sequentially or simultaneously, to simulate the absorption of more than one wavelength, and to various degrees. It is to be noted that, for simplicity, various optical components which would normally be used in the testing process, are not illustrated.

Figure 4:
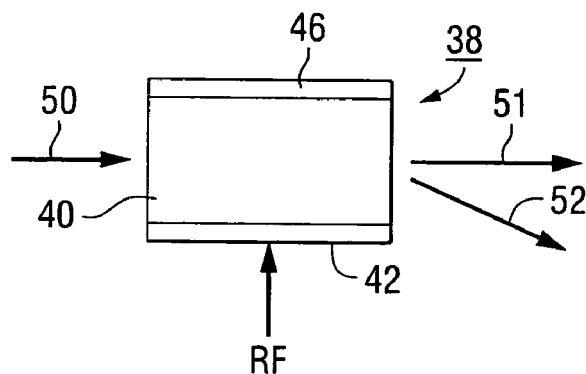
FIG. 4 is a view of a component used in the arrangement of FIG. 3.

Basic operation of the AOTF 38 is illustrated in FIGS. 4 and 5A to 5C. In FIG. 4, input radiation along path 50 enters the crystal 40 and, in the absence of an applied RF signal exits either along the path 51 or 52, depending upon the crystal orientation. Conventionally, one of these paths is known as the zero order and the other as the first order.

Figure 5A:
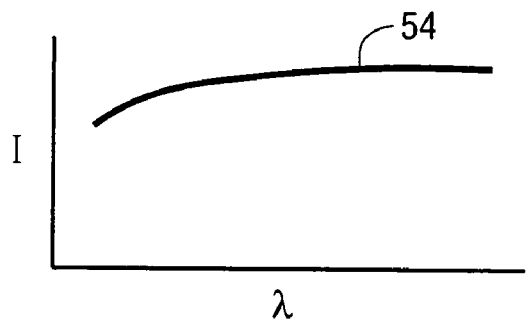
FIGS. 5A, 5B and 5C are waveforms to aid in an understanding of the component of FIG. 4.
Figure 5B:
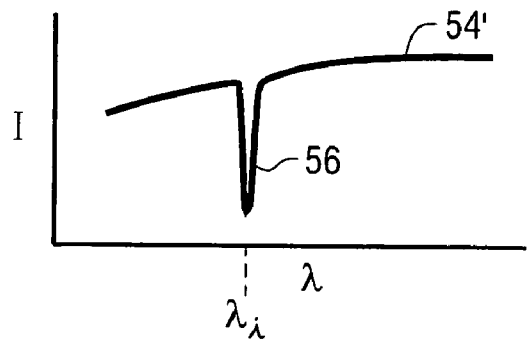
Figure 5C:
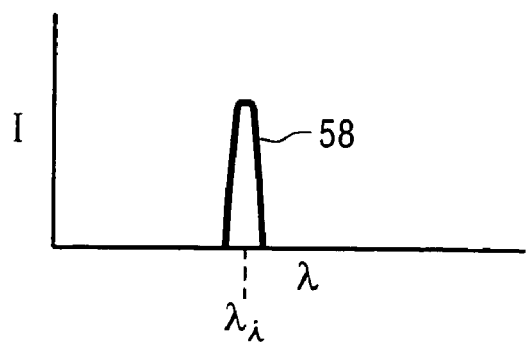

In FIG. 5A, characteristic curve 54 represents the intensity of the input radiation as a function of wavelength. Let it be assumed that crystal 40 is oriented such that, in the absence of any applied RF signal, all entering radiation passes through the crystal 40 and exits along a desired path 51. If an RF signal corresponding to wavelength $\lambda_i$ is now applied, wavelength $\lambda_i$ will be deflected to now exit along the path 52 such that it will not be transmitted along the desired path. The characteristic curve 54 is therefore modified, as represented by curve 54' in FIG. 5B, to include a notch portion 56, indicative of the non-transmitted wavelength. In FIG. 5C curve 58 represents the filtered wavelength $\lambda_i$.

In an alternate mode of operation the crystal orientation may be such that in the absence of any applied RF signal, all of the entering radiation will exit along the path 52 and when an appropriate RF signal is applied, corresponding to a particular wavelength, that wavelength will be deflected to exit along the path 51. In operation, more than one wavelength at a time may be deflected with the intensity of deflection being a function of the power level of the applied RF signal.

Figure 6:
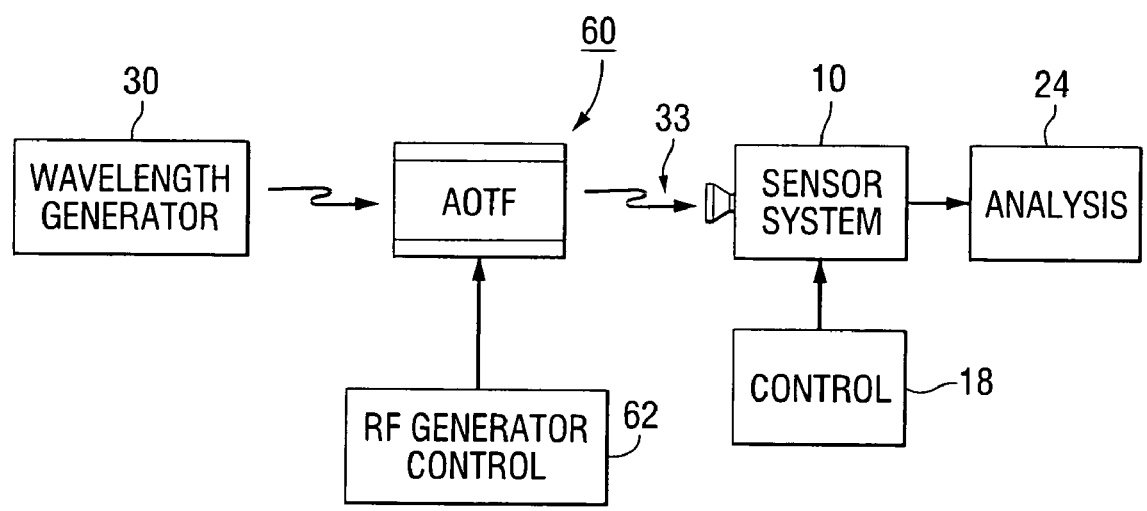
FIG. 6 is a block diagram of another embodiment of the hyperspectral imaging system testing apparatus.

In FIG. 6, the method of operation is such, that the spectrometer 34 of FIG. 3 may be eliminated. An AOTF 60 is provided having a crystal orientation such that all radiation received from wavelength generator 30 is, in the absence of any applied RF signal from RF generator control 62, transmitted to sensor system 10 via transmission path 33. That is, the radiation emanating from AOTF 60 and directed towards sensor system 10 includes all of the generated radiation and is described by curve 54 of FIG. 5A.

With the previous wavelength example, sensor system 10 will examine only wavelengths $\lambda_{12}$, $\lambda_{85}$, $\lambda_{115}$ and $\lambda_{400}$ out of the totality of wavelengths received, to obtain a baseline reading. Thereafter to simulate the previously described atmospheric absorption, RF generator control 62 will apply the appropriate RF signal to deflect wavelength $\lambda_{115}$, (or a plurality of wavelengths, as the case may be) corresponding to total or partial absorption, whereby the sensor system 10 may be evaluated under such condition.

Thus, the effect of various atmospheric absorptions on a spectral imaging system may be determined in the lab without the necessity of actual field testing in the presence of a particular gas, which may or may not be present when a field test is to take place.

Figure 7:
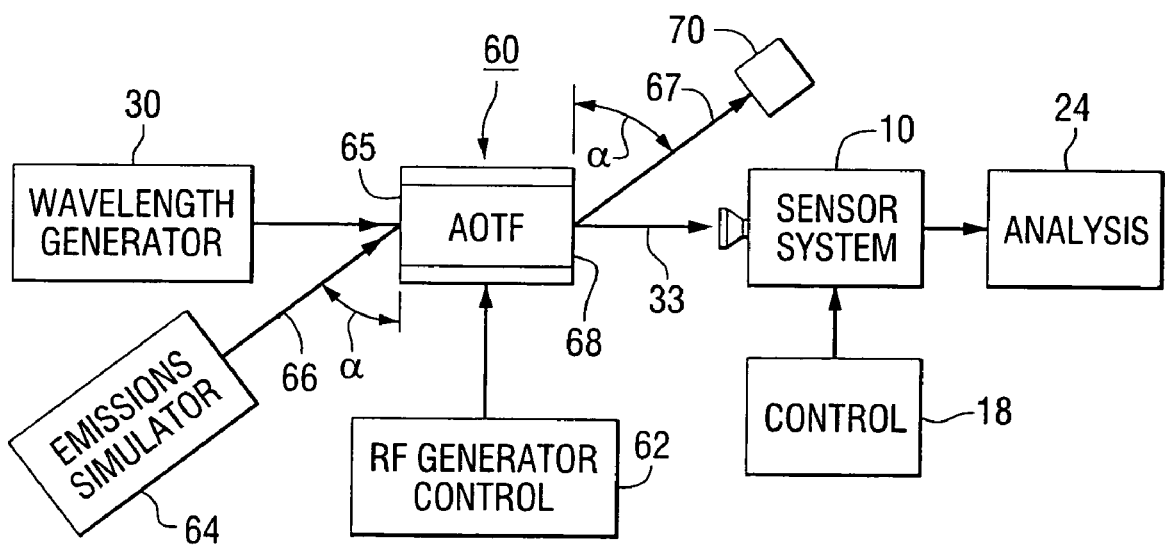
FIG. 7 is a block diagram of one embodiment of the present invention.

For a comprehensive testing system it is also necessary to take into account not only various atmospheric absorptions but various atmospheric emissions, as well. Such emissions may emanate from, for example, a vehicle exhaust system, smokestack emissions or from any other target which produces hot gases. FIG. 7 illustrates an embodiment of the invention which can simulate these emissions, for testing purposes.

FIG. 7 is similar to FIG. 6, however with the addition of emissions simulator 64. The emissions simulator 64 may be similar to wavelength generator 30 in being comprised of an X-Y array of IR broadband emitters, individually addressable to create a predetermined pattern of IR radiation.

The radiation output from emissions simulator 64 is directed toward the input face 65 of AOTF 60 along path 66, lying at an angle $\alpha$ with respect to the input face 65. In the absence of any applied RF signal from RF generator control 62, the radiation traveling along path 66 emerges from the AOTF 60 via the path 67, also at an angle $\alpha$, with respect to the output face 68.

FIG. 7 also illustrates an optional piece of equipment in the form of absorber 70. Absorber 70 functions as a beam dump and prevents any radiation along path 67 from reaching the sensor system 10 by reflection from walls, or other objects which may be located in the testing facility. It is to be noted that such absorber may also be used in the previously described arrangements.

In a typical operational test, wavelength generator 30 projects a desired target image to the sensor system 10 via the AOTF and transmission path 33. Let it be assumed that the selected target also produces a hot gas emission of one or more wavelengths. Emissions simulator 64 is operable to project a broadband IR signal having the shape of an expected exhaust cloud at a predetermined position in the X-Y array corresponding to where the exhaust would appear relative to the target image produced by wavelength generator 30.

With the wavelength or wavelengths of the emission being known, the appropriate RF signal or signals may be supplied by RF generator control 62 to cause the wavelength or wavelengths representing the emission to be diverted to the transmission path 33. Accordingly, the sensor system 10 receives a target image, upon which is superimposed a hot gas emission at the proper location relative to the target so that the results my be properly analyzed by the analysis circuit 24.

The foregoing detailed description merely illustrates the principles of the invention. It will thus be appreciated that those skilled in the art will be able to devise various arrangements which, although not explicitly described or shown herein, embody the principles of the invention and are thus within its spirit and scope.

What is claimed is:

1. Testing apparatus for testing a spectral imaging system, comprising:
   a wavelength generator for providing radiation over a broad spectrum in a predetermined pattern representing a target;
   an electronically controlled selective filter arrangement positioned relative to said wavelength generator to pass only certain wavelengths of radiation to said spectral imaging system along a transmission path;
   said electronically controlled selective filter arrangement including a control to remove or add a predetermined portion of one or more selected wavelengths from, or to, said transmission path;
   an emissions simulator operable to generate radiation over a broad spectrum in a predetermined chosen pattern representing emissions from said target;
   said emissions simulator being positioned to project its radiation of said chosen pattern, to said electronically controlled selective filter arrangement;
   said control being operable to select a predetermined one or more wavelengths from said emissions simulator for transmission along said transmission path.

2. Apparatus according to claim 1 wherein:
   said electronically controlled selective filter arrangement includes an AOTF in the radiation path between said wavelength generator and said spectral imaging system and between said emissions simulator and said spectral imaging system;
   said AOTF including an RF generator control circuit for supplying said AOTF with one or more predetermined RF signals;
   said AOTF being operable, in the absence of any applied RF control signal, to transmit, along said transmission path, all of said wavelengths provided by said wavelength generator and none of said wavelengths provided by said emissions simulator;
   said RF generator control circuit being operable to supply said AOTF with one or more predetermined RF signals to cause a predetermined deflection of corresponding one more wavelengths from said emissions simulator into said transmission path.

3. Apparatus according to claim 1 wherein:
   said spectral imaging system is a hyperspectral imaging system; and
   said wavelength generator and said emissions simulator generate radiation in the IR region.

4. A method of testing a spectral imaging system comprising the steps of:
   generating a broad spectrum of wavelengths in a predetermined pattern of a desired target and directed toward said spectral imaging system along a transmission path;
   interposing an electronically controlled selective filter arrangement to pass only certain said wavelengths to said spectral imaging system along a transmission path;
   controlling said selective filter arrangement to remove or add a predetermined portion of one or more selected wavelengths from said transmission path;
   generating an additional broad spectrum of wavelengths in a predetermined pattern representing an emission pattern from said target, and projected to said selective filter arrangement;
   controlling said selective filter arrangement to select one or more wavelengths from said additional broad spectrum of wavelengths for transmission along said transmission path.

5. A method according to claim 4 which includes:
   passing only certain ones of said wavelengths which will be used by said spectral imaging system in a target determination process.

6. A method according to claim 4 which includes:
interposing an AOTF in the wavelength path;
controlling said AOTF so as to remove a predetermined portion of one or more wavelengths representing said target, from said transmission path and to add one or more wavelengths representing said target emission pattern, to said transmission path.

7. A method according to claim 4 wherein:
the spectral imaging system is a hyperspectral imaging system; and which includes the step of,
generating a broad spectrum and additional broad spectrum of IR wavelengths.

* * * * *